(12) United States Patent
Pfundtner et al.

(10) Patent No.: US 10,610,660 B2
(45) Date of Patent: Apr. 7, 2020

(54) PROVIDING SENSORY STIMULATION BASED ON SLOW WAVE PERIODICITY

(71) Applicant: KONINKLIJKE PHILIPS N.V., Eindhoven (NL)

(72) Inventors: Stefan Pfundtner, Eindhoven (NL); Gary Nelson Garcia Molina, Madison, WI (US); Tsvetomira Kirova Tsoneva, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 324 days.

(21) Appl. No.: 15/565,252

(22) PCT Filed: Apr. 14, 2016

(86) PCT No.: PCT/EP2016/058203
§ 371 (c)(1),
(2) Date: Oct. 9, 2017

(87) PCT Pub. No.: WO2016/166202
PCT Pub. Date: Oct. 20, 2016

(65) Prior Publication Data
US 2018/0078734 A1 Mar. 22, 2018

Related U.S. Application Data

(60) Provisional application No. 62/147,332, filed on Apr. 14, 2015.

(30) Foreign Application Priority Data

May 1, 2015 (EP) ..................................... 15166099

(51) Int. Cl.
*A61M 21/02* (2006.01)
*A61B 5/048* (2006.01)
(Continued)

(52) U.S. Cl.
CPC ............. *A61M 21/02* (2013.01); *A61B 5/048* (2013.01); *A61B 5/0476* (2013.01);
(Continued)

(58) Field of Classification Search
CPC ............ A61M 21/02; A61M 2230/005; A61M 2021/0005; A61M 2021/0083;
(Continued)

(56) References Cited

U.S. PATENT DOCUMENTS 8,948,862 B2   2/2015   Hamaguchi et al.
2008/0081941 A1   4/2008   Tononi
(Continued)

FOREIGN PATENT DOCUMENTS

CN   201529321 U   7/2010
CN   102043385 A   5/2011
(Continued)

OTHER PUBLICATIONS

G. Tononi and C. Cirelli, "Sleep function and synaptic homeostasis.," Sleep Med. Rev., vol. 10, No. 1, pp. 49-62, Feb. 2006.
(Continued)

*Primary Examiner* — Christine H Matthews (57) ABSTRACT

The present disclosure pertains to a system configured to provide sensory stimulation to a subject during a sleep session. The system includes one or more sensory stimulators configured to provide sensory stimulation to the subject; one or more sensors configured to generate output signals conveying information related to brain activity of the subject; and one or more processors configured to detect individual slow waves in the subject; control the one or more sensory stimulators to provide sensory stimulation to the subject based on the detected individual slow waves; predict a timing for occurrence of a predicted slow wave based on the previously detected individual slow waves; and respon-
(Continued)

sive to not detecting the predicted slow wave at the predicted timing control the one or more sensory stimulators to provide sensory stimulation at the predicted timing for occurrence of the predicted slow wave.

15 Claims, 10 Drawing Sheets

(51) Int. Cl.
*A61B 5/00* (2006.01)
*A61B 5/0476* (2006.01)
*A61M 21/00* (2006.01)
*A61B 5/0484* (2006.01)

(52) U.S. Cl.
CPC .......... *A61B 5/4812* (2013.01); *A61B 5/6803* (2013.01); *A61B 5/0484* (2013.01); *A61B 5/4064* (2013.01); *A61M 2021/0005* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2205/3303* (2013.01); *A61M 2230/10* (2013.01)

(58) Field of Classification Search
CPC ...... A61M 2205/3303; A61M 2205/52; A61B 5/4812; A61B 5/04012; A61N 1/36078
See application file for complete search history.

(56) References Cited

U.S. PATENT DOCUMENTS

| | | |
|---|---|---|
| 2012/0251989 A1 | 10/2012 | Wetmore et al. |
| 2014/0031712 A1 | 1/2014 | Herskovitz et al. |
| 2015/0273177 A1 | 10/2015 | Iizuka |

FOREIGN PATENT DOCUMENTS

| | | |
|---|---|---|
| JP | 2014083657 A | 5/2014 |
| WO | 2014170781 A1 | 10/2014 |
| WO | 2014170881 A1 | 10/2014 |

OTHER PUBLICATIONS

B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.
M. Steriade, A. Nuñez, and F. Amzica, "A Novel Slow (<1 Hz) Oscillation of Neocortical Neurons in vivo: Depolarizing and Hyperpolarizing Components," J. Neurosci., vol. 13, No. 8, pp. 3252-3265, 1993.
H.-V. V Ngo, T. Martinetz, J. Born, and M. Molle, "Auditory Closed-Loop Stimulation of the Sleep Slow Oscillation Enhances Memory," Neuron, vol. 78, No. May, pp. 1-9, 2013.
M. Massimini, R. Huber, F. Ferrarelli, S. Hill, and G. Tononi, "The sleep slow oscillation as a traveling wave," J. Neurosci., vol. 24, No. 31, pp. 6862-6870, Aug. 2004.
S. G. Roux, T. Cenier, S. Garcia, P. Litaudon, and N. Buonviso, "A wavelet-based method for local phase extraction from a multi-frequency oscillatory signal.," J. Neurosci. Methods, vol. 160, No. 1, pp. 135-143, Feb. 2007.

PROVIDING SENSORY STIMULATION BASED ON SLOW WAVE PERIODICITY

CROSS-REFERENCE TO PRIOR APPLICATIONS

This application is the U.S. National Phase application under 35 U.S.C. § 371 of International Application Serial No. PCT/EP2016/058203, filed on 14 Apr. 2016, which claims the benefit of U.S. Application Ser. No. 62/147,332, filed on 14 Apr. 2015 and European Application No. 15166099.0, filed on 1 May 2015. These applications are hereby incorporated by reference herein.

FIELD OF THE INVENTION

The present disclosure pertains to a system and method for providing sensory stimulation based on slow wave periodicity.

BACKGROUND OF THE INVENTION

Systems for monitoring sleep are known. Determining sleep stages during sleep is known. Sensory stimulation during sleep is known.

SUMMARY OF THE INVENTION

However, sensory stimulation during sleep is often applied continuously and/or at intervals that do not correspond to the intrinsic slow-wave periodicity of a subject. The present disclosure overcomes deficiencies in prior art systems. The invention is defined by the independent claims. The dependent claims define advantageous embodiments.

One embodiment relates to a system configured to provide sensory stimulation to a subject during a sleep session. The system includes one or more sensory stimulators, one or more sensors, one or more processors, and/or other components. The one or more sensory stimulators may be configured to provide sensory stimulation to the subject. The one or more sensors may be configured to generate output signals conveying information related to brain activity of the subject. The one or more processors may be configured to detect individual slow waves in the subject based on the output signals; control the one or more sensory stimulators to provide sensory stimulation to the subject with a timing based on the detected individual slow waves; predict a timing for occurrence of a predicted slow wave based on previous ones of the detected individual slow waves; responsive to not detecting the predicted slow wave at the predicted timing, control the one or more sensory stimulators to provide sensory stimulation to the subject at the predicted timing for occurrence of the predicted slow wave.

Another embodiment relates to a method for providing sensory stimulation to a subject during a sleep session using a determination system. The system includes one or more sensory stimulators, one or more sensors, one or more processors, and/or other components. The method includes generating output signals conveying information related to brain activity of the subject with the one or more sensors; detecting, with the one or more processors, individual slow waves in the subject based on the output signals; controlling, with the one or more processors, the one or more sensory stimulators to provide sensory stimulation to the subject with a timing based on the detected individual slow waves; predicting, with the one or more processors, a timing for occurrence of a predicted slow wave based on previous ones of the detected individual slow waves; and responsive to not detecting the predicted slow wave at the predicted timing, controlling the one or more sensory stimulators, with the one or more processors, to provide sensory stimulation to the subject at the predicted timing for occurrence of the predicted slow wave.

Still another embodiment relates to a system configured to determine timing of sensory stimulation delivered to a subject during a sleep session. The system includes means for providing sensory stimulation to the subject; means for generating output signals conveying information related to brain activity of the subject; means for detecting individual slow waves in the subject based on the output signals; means for controlling the means for providing sensory stimulation to provide sensory stimulation to the subject with a timing based on the detected individual slow waves; means for predicting a timing for occurrence of a predicted slow wave based on previous ones of the detected individual slow waves; and means for controlling the means for providing sensory stimulation to provide sensory stimulation to the subject at the predicted timing for occurrence of the predicted slow wave responsive to not detecting the predicted slow wave at the predicted timing.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

Figure 1:
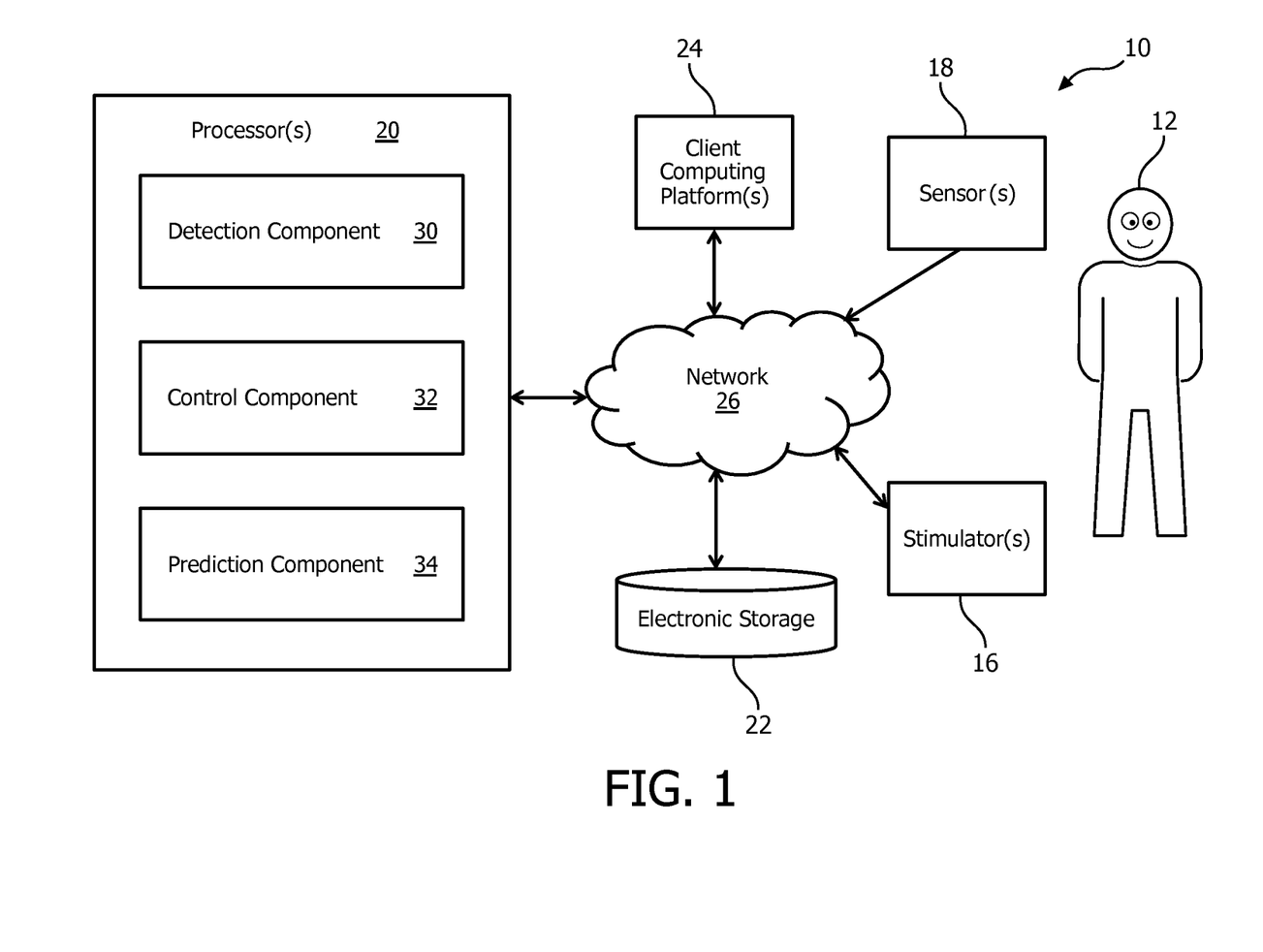
FIG. 1 is a schematic illustration of a system configured to determine timing of sensory stimulation delivered to a subject.

FIG. 1 is a schematic illustration of a system 10 configured to provide sensory stimulation to a subject 12 during a sleep session. Sensory stimulation (e.g., auditory stimulation) during sleep may enhance and/or induce sleep slow-waves and increase the restorative value of sleep. System 10 may be configured to monitor subject 12 electroencephalograms (EEG) during sleep and deliver auditory stimulation to enhance sleep slow waves without causing arousals. In some embodiments, system 10 comprises one or more of sensory stimulator(s) 16, sensor(s) 18, a processor 20, electronic storage 22, client computing platform(s) 24, a network 26, and/or other components. System 10 may be configured to detect individual slow waves in the subject. System 10 may be configured to control the stimulators 16 to provide sensory stimulation to the subject with a timing based on the detected individual slow waves. System 10 may be configured to predict a timing for occurrence of one or more predicted slow waves based on the previously detected individual slow waves. System 10 may be configured to, responsive to not detecting a predicted slow wave at the predicted timing, control the sensory stimulator(s) 16 to provide sensory stimulation to the subject at the predicted timing for occurrence of the predicted slow wave.

Figure 2A:
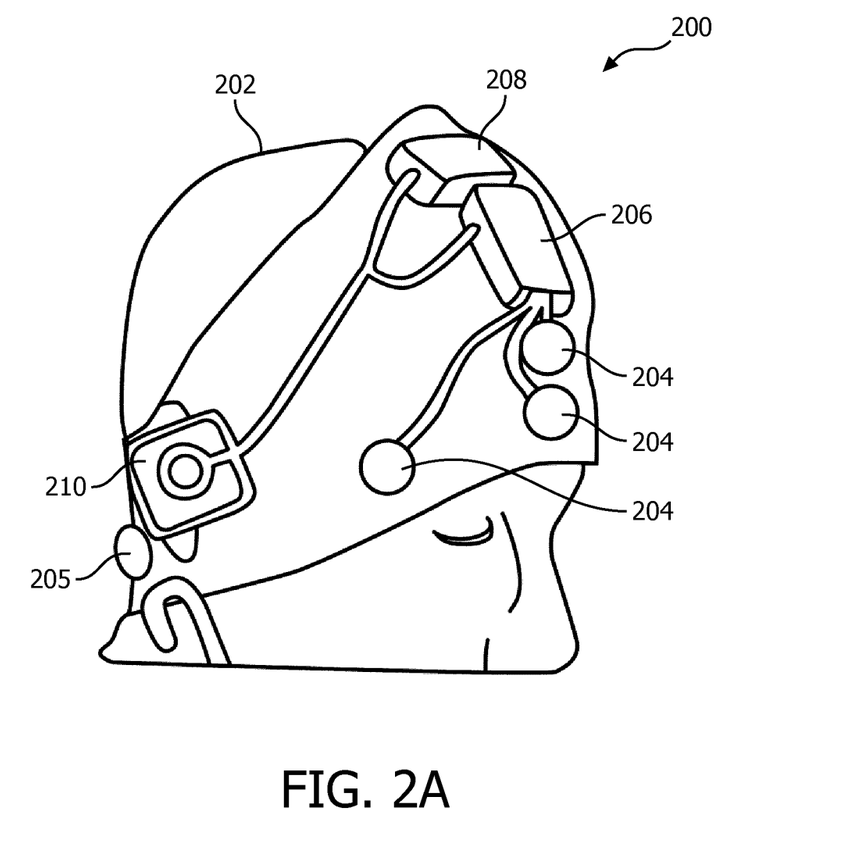
FIG. 2A illustrates example operations performed by detection component to detect a slow wave, in accordance with one or more embodiments.

In FIG. 1, sensory stimulator(s) 16, sensor(s) 18, processor 20, electronic storage 22, and client computing platform(s) 24 are shown as separate entities. This is not intended to be limiting. Some and/or all of the components of system 10 and/or other components may be grouped into one or more singular devices. For example, FIG. 2A illustrates a headband 200 worn by a subject 202. Headband 200 includes sensing electrodes 204, a reference electrode 205, one or more devices associated with an EEG 206, a wireless audio device 208, and one or more audio speakers 210. Audio speakers 210 may be located in and/or near the ears of subject 202 and/or in other locations. The reference electrode 205 may be located behind the ear of subject 202, and/or in other locations. In the example shown in FIG. 2A, sensing electrodes 204 may be configured to generate output signals conveying information related to brain activity of subject 202, and/or other information. The output signals may be transmitted to a computing device (e.g., a bedside laptop) wirelessly and/or via wires. Acoustic stimulation may be delivered to subject 202 via wireless audio device 208 and/or speakers 210. Sensing electrodes 204, reference electrode 205, and devices 206 may be represented, for example, by sensor(s) 18 in FIG. 1. Wireless audio device 208 and speakers 210 may be represented, for example, by sensory stimulator(s) 16 shown in FIG. 1. In this example, the computing device (not shown in FIG. 2A) may include processor 20, electronic storage 22, client computing platform(s) 24, and/or other components of system 10 shown in FIG. 1.

Returning to FIG. 1, sensory stimulator(s) 16 is configured to provide sensory stimulation to subject 12. Sensory stimulator(s) 16 may be configured to provide sensory stimulation to subject 12 prior to a sleep session, during a current sleep session, after a sleep session, and/or at other times. For example, sensory stimulator(s) 16 may be configured to provide sensory stimulation to subject 12 during slow wave sleep in a sleep session. Sensory stimulator(s) 16 may be configured to provide sensory stimulation to subject 12 during a sleep session to induce sleep slow waves and/or enhance sleep slow waves in subject 12. In some embodiments, sensory stimulator(s) 16 may be configured to induce and/or enhance sleep slow waves through non-invasive brain stimulation and/or other methods. Sensory stimulator(s) 16 may be configured to induce and/or enhance sleep slow waves through non-invasive brain stimulation using sensory stimulation including odors, sounds, visual stimulation, touches, tastes, and/or other stimulation. In some embodiments, sensory stimulator (s) 16 may be configured to induce and/or enhance sleep slow waves via auditory stimulation of subject 12. Examples of sensory stimulator(s) 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

In some embodiments, sensory stimulations, time interval between the sensory stimulations, intensity of the sensory stimulations, volume of the sensory stimulations, and/or other functions of the sensory stimulator(s) may be adjusted by input from users, subjects, one or more component within or outside of system 10. Adjustments to one or more functions (e.g., time interval, intensity, volume, etc.) of the sensory stimulator(s) may be based on information from individual subjects, information from individual users (e.g., healthcare professionals, caregivers, etc.), individual therapies, manufacturer settings, and/or other information. For example, volume of auditory stimulator(s) may be adjusted between upper and lower thresholds. The upper and lower thresholds for the volume may be determined for each subject based on previous tests. For example, to set the upper threshold for a given subject, the subject may be presented with progressively increasing tones and asked to estimate the volume that the subject thinks can wake him up.

Sensor(s) 18 is configured to generate output signals conveying information related to brain activity of subject 12. The brain activity of subject 12 may correspond to sleep states and/or other characteristics of subject 12. Sleep states may include, correspond to, and/or be indicative of sleep stages. The brain activity of subject 12 may be associated with sleep states and/or sleep stages that include, correspond to, and/or be indicative of rapid eye movement (REM) sleep, non-rapid eye movement (NREM) sleep (e.g., slow wave sleep), and/or other sleep states. Sensor(s) 18 may comprise one or more sensors that measure such parameters directly. For example, sensor(s) 18 may include electrodes configured to detect electrical activity along the scalp of subject 12 resulting from current flows within the brain of subject 12. Sensor(s) 18 may comprise one or more sensors that generate output signals conveying information related to brain activity of subject 12 indirectly. For example, one or more sensors 18 may generate an output based on a heart rate of subject 12 (e.g., sensor(s) 18 may be a heart rate sensor located on the chest of subject 12, and/or be configured as a bracelet on a wrist of subject 12, and/or be located on another limb of subject 12), movement of subject 12 (e.g., sensor(s) 18 may include a bracelet around the wrist and/or ankle of subject 12 with an accelerometer such that sleep may be analyzed using actigraphy signals), respiration of subject 12, and/or other characteristics of subject 12. Although sensor(s) 18 is illustrated at a single location near subject 12, this is not intended to be limiting. Sensor(s) 18 may include sensors disposed in a plurality of locations, such as for example, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator(s) 16, sensor(s) 18), or processor 20 may represent processing functionality of a plurality of devices operating in coordination.

As shown in FIG. 1, processor 20 is configured to execute one or more computer program components. The one or more computer program components may comprise one or more of a detection component 30, a control component 32, a prediction component 34, and/or other components. Processor 20 may be configured to execute components 30, 32, 34, and/or other components by software; hardware; firmware; some combination of software, hardware, and/or firmware; and/or other mechanisms for configuring processing capabilities on processor 20.

It should be appreciated that although components 30, 32, and 34 are illustrated in FIG. 1 as being co-located within a single processing unit, in embodiments in which processor 20 comprises multiple processing units, one or more of components 30, 32, 34, and/or other components may be located remotely from the other components. The description of the functionality provided by the different components 30, 32, 34, and/or other components described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, processor 20 may be configured to execute one or more additional components that may perform some or all of the functionality attributed below to one of components 30, 32, and/or 34

Detection component 30 may be configured to detect sleep states and/or sleep stages in subject 12. In some embodiments, detection component 30 may be configured to detect sleep states and/or sleep stages based on the output signals from sensor(s) 18, and/or based on other information received from other components within or outside of system 10. Sleep states in subject 12 may include rapid eye movement (REM) sleep state, non-rapid eye movement (NREM) sleep state, and/or other sleep states. Sleep stages in subject 12 may include NREM sleep stages (e.g., N1, N2, and/or N3).

Figure 2B:
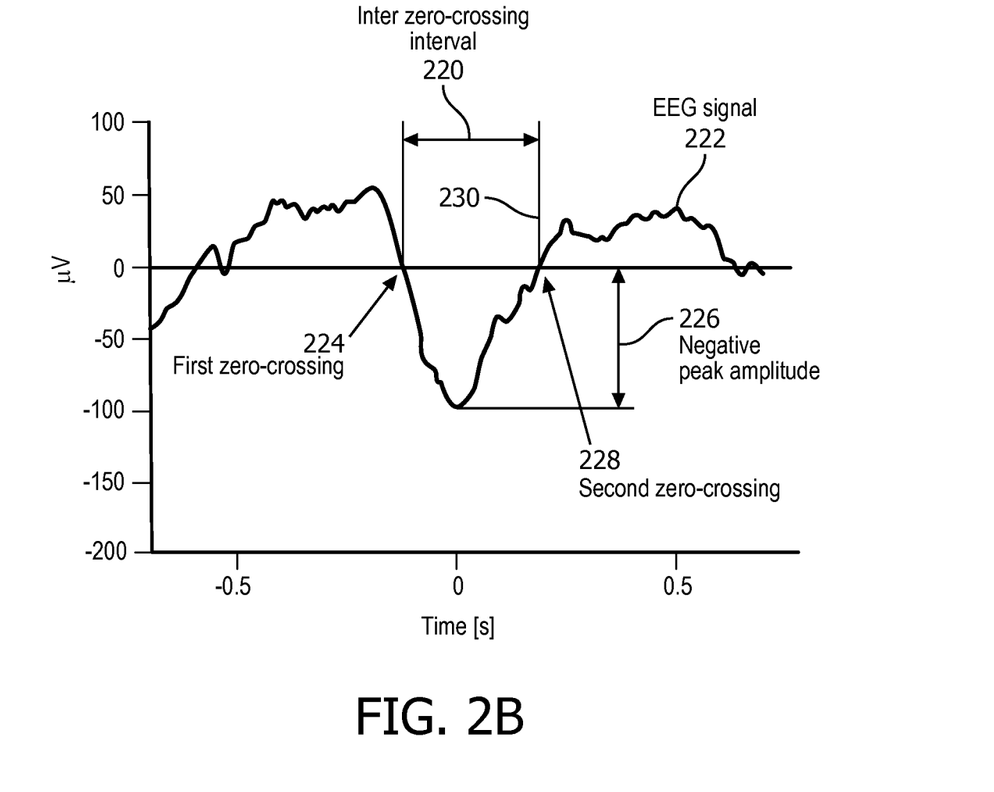
FIG. 2B illustrates example operations performed by detection component to detect a slow wave, in accordance with one or more embodiments.

In some embodiments, detection component 30 may configured to detect one or more individual slow waves in subject 12. FIG. 2B illustrates example operations performed by detection component 30 to detect a slow wave. Slow waves correspond to stage three (N3) in NREM sleep stages. This period of sleep is referred to as slow-wave sleep because the EEG activity is synchronized, reflecting the brain's Cortex bi-stability state typical of NREM sleep. The bi-stability state is such that neurons in the brain's cortex alternate between ON and OFF periods with a periodicity of approximately 1 second, producing typically slow waves with a frequency of approximately 1 Hz and relatively high amplitude. In some embodiments, detection component 30 may be configured to detect different phases of a given slow wave. For example, detection component 30 may be configured to detect a down phase of a given slow wave. The down phase corresponding to the first section of the wave (hyperpolarizing phase), which is an inhibition period, leading to an OFF state in which the neurons in the neocortex are silent. In some embodiments, detection component 30 may be configured to detect an up-state of a given slow wave. The up-state being the second section of the wave (depolarizing phase), which is an excitation period during which the neurons fire briefly at a high rate.

FIG. 2B and the corresponding description below should not be considered limiting. Detection component 30 may detect slow wave sleep by any method that allows system 10 to function as described herein. In the example shown in FIG. 2B, detection of slow-waves is done by detecting zero-crossings of an EEG signal 222. A first, negative, zero-crossing, shown at 224, is detected. The amplitude of the most prominent negative peak 226 of the EEG signal 222 following the first negative zero-crossing 224 is compared to a pre-established detection threshold (e.g. −40 microvolt). If the absolute value of the amplitude of the negative peak 226 exceeds the threshold (also in absolute value), then a second, positive, zero-crossing 228 is detected. If the duration between the first and second zero-crossings (inter zero-crossing interval 220) is within a given duration interval (e.g. from 200 milliseconds to 800 milliseconds), then the event corresponds to a detected slow-wave. In FIG. 2B, 230 corresponds to the up-state of the detected slow wave.

Figure 3A:
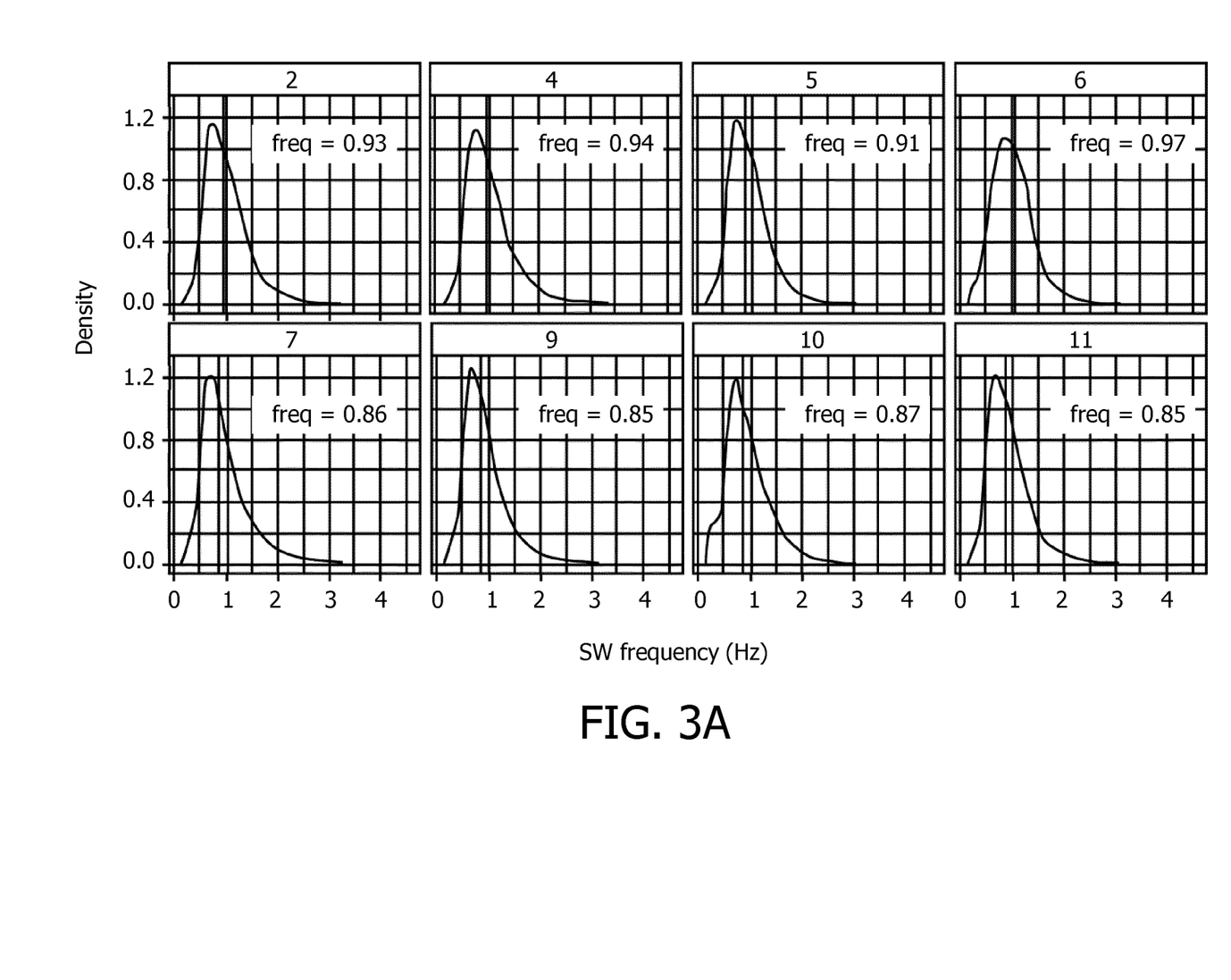
FIG. 3A illustrates an example of slow waves detected in different subjects.
Figure 3B:
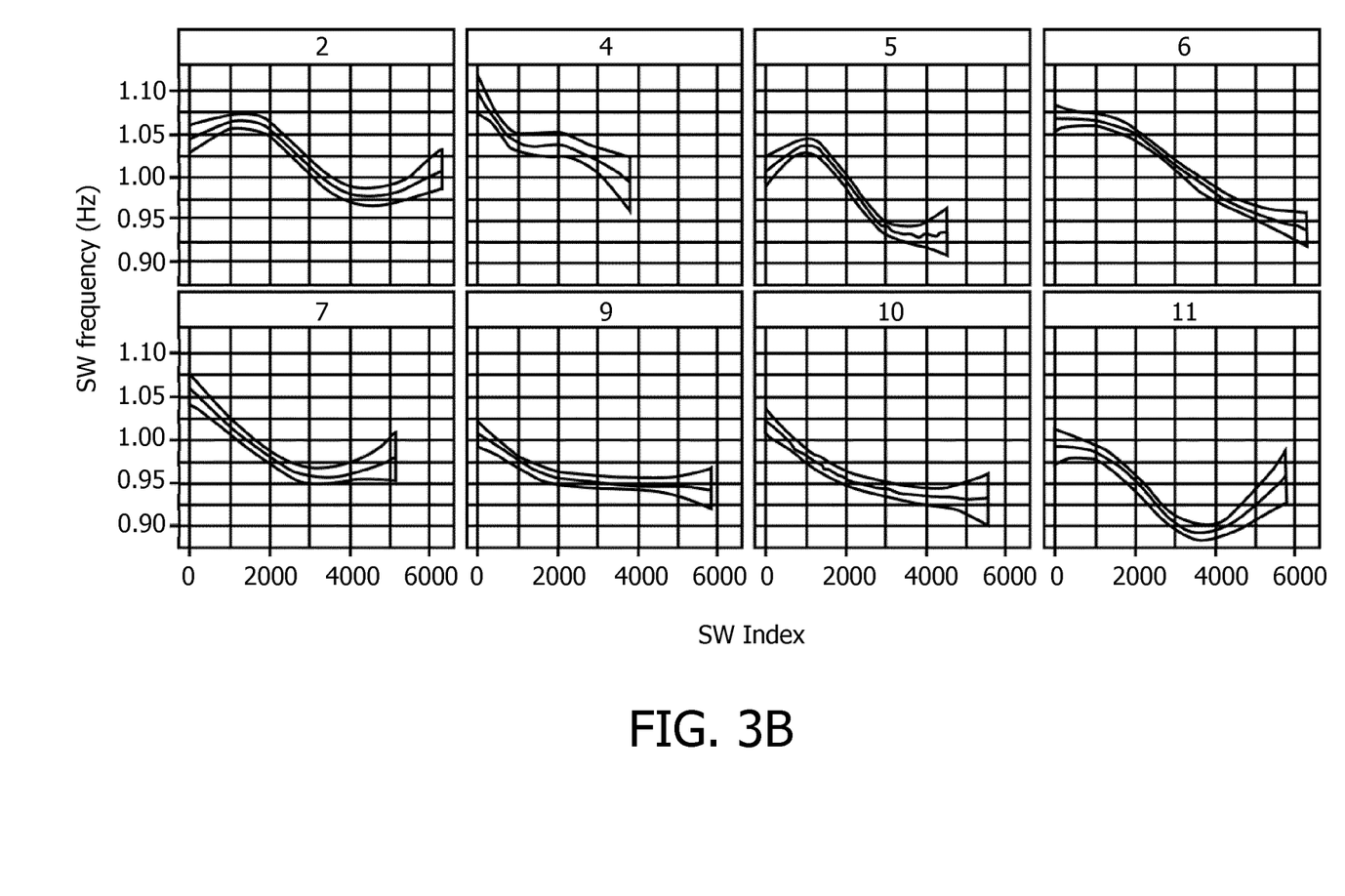
FIG. 3B shows different individual slow waves detected in a subject at different times of a given night.

Individual slow waves detected by detection component 30 may vary by subject. Individual slow waves detected in different subjects may vary in frequency, amplitude, and/or other slow wave characteristics. FIG. 3A shows an example of slow waves detected in different subjects with the slow waves having different frequencies. Individual slow waves detected, with detection component 30, in a given subject, may vary depending on the time of the night at which they are detected. Individual slow waves detected in a subject may vary in frequency, amplitude, and/or other slow wave characteristics. FIG. 3B shows different individual slow waves with different frequencies, detected in subject 12 at different times of a given night.

Returning to FIG. 1, control component 32 is configured to control sensory stimulator(s) 16 to provide sensory stimulation to subject 12. Control component 32 may be configured to control sensory stimulator(s) 16 to provide sensory stimulation to subject 12 prior to a sleep session, during a current sleep session, after a sleep session, and/or at other times. Control component 32 may be configured to control sensory stimulator(s) 16 to provide sensory stimulation during sleep states and/or sleep stages detected by detection component 30. For example, sensory stimulator(s) 16 may be configured to provide sensory stimulation to subject 12 during slow wave sleep in a sleep session. In some embodiments, control component 32 may be configured to control stimulator(s) 16 to provide sensory stimulation at a timing based on the detected individual slow waves detected by detection component 30.

In some embodiments, system 10 may be configured to estimate the effect of sensory stimulation on the sleep state of the subject in real or near-real time. Control component 32 may be configured to control sensory stimulator(s) 16 to adjust the sensory stimulation based on the estimated effect on the subject. Sensory stimulation may be adjusted between an upper threshold and a lower threshold. The upper thresholds and a lower threshold may be determined based on subject 12, and/or based on other parameters determined by a user (e.g., healthcare professional, care giver, etc.), and/or one or more components within or outside of system 10.

For example, control component 32 may be configured to control an auditory stimulator to provide auditory stimulation to subject 12 at timings of detected and/or predicted slow waves (as described herein below). System 10 may be configured to estimate the effect of the auditory stimulation on the subject 12. System 10 may estimate the effect of the auditory stimulation using one or more components within or outside of system 10. System 10 may be configured to estimate the effect of the auditory stimulation by assessing the slow wave enhancement in real time and/or near-real time. System 10 may be configured to estimate the effect of the auditory stimulation by assessing subject 12 (e.g., monitoring subject 12 arousals). System 10 may be configured to adjust the volume of the auditory stimulation in real or near real time based on the effect of the auditory stimulation on the slow waves, and/or subject 12. In some embodiments, system 10 may be configured to adjust the volume between an upper threshold and a lower threshold. The upper and lower thresholds may be determined based on subject 12. For example, a lower threshold for subject 12 may be determined by performing perceptual tests on subject 12, the lower threshold being the auditory perception threshold. The upper threshold for subject 12 may be determined by performing tests, on subject 12, during which subject 12 is presented with progressively increasing tones and asked to estimate the volume that subject 12 thinks will wake him up. It is to be noted that other techniques may be used to determine the upper and lower thresholds.

By way of non-limiting example, in an operation corresponding to one or more embodiments, control component 32 is configured to control stimulator(s) to provide sensory stimulation to subject 12 at the timing of individual slow waves detected by detection component 30. Detection component 30 is configured to detect arousals is subject 12 in real or near-real time. If arousal is detected during stimulation, control component 32 controls stimulator(s) 16 to stop stimulation, and wait for the next detected slow wave to provide stimulation. If arousal is detected outside of the stimulation period, control component 32 controls stimulator(s) 16 to delay stimulation of subject 12.

Figure 4:
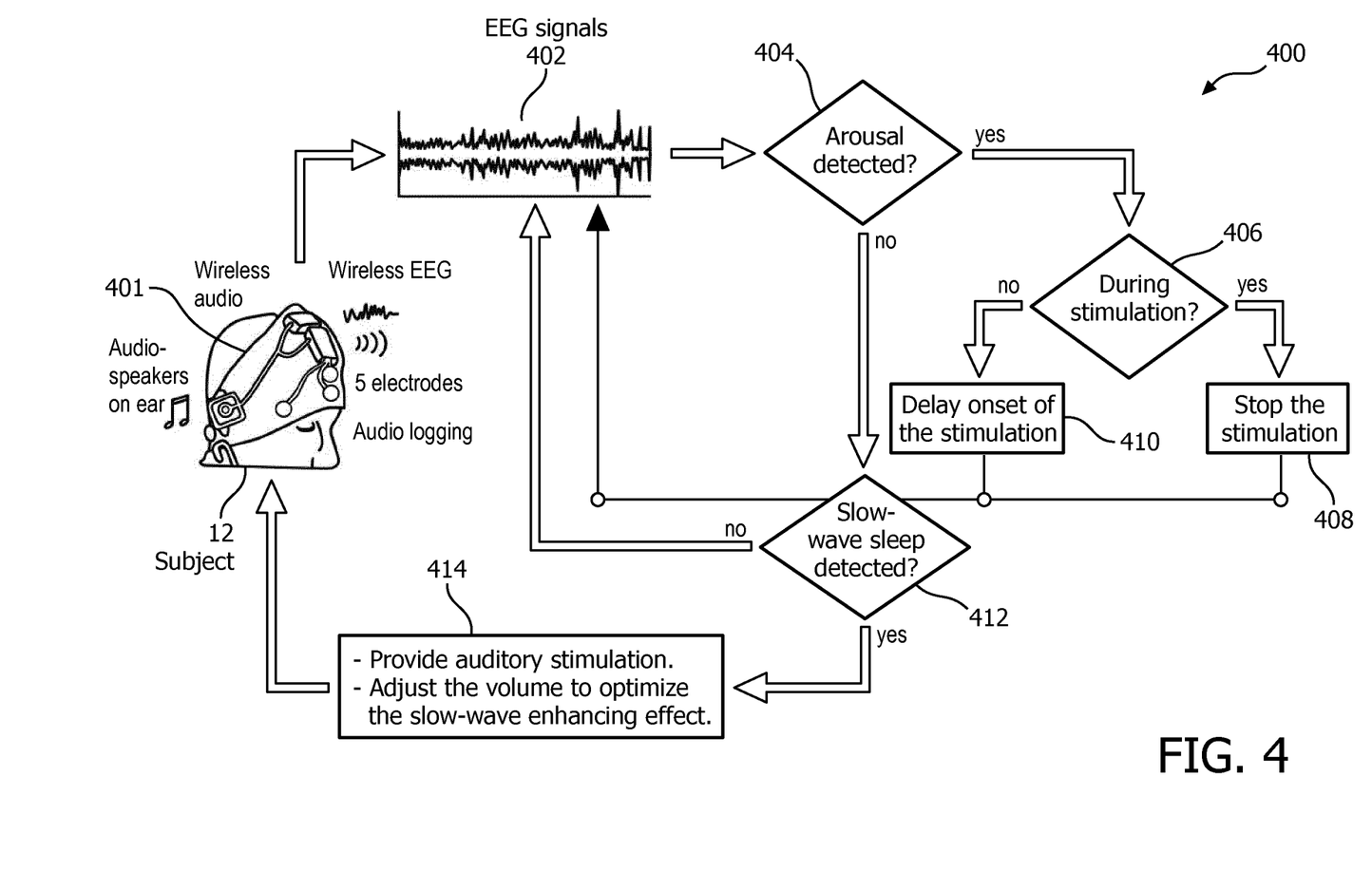
FIG. 4 illustrates example operations performed by one or more components of system 10, in accordance with one or more embodiments.

FIG. 4 illustrates example operations 400 performed by system 10 to detect slow wave sleep, and provide auditory stimulation to subject 12. Sensory stimulator 401, shown in FIG. 4, may be similar to stimulator 200 described in FIG. 2A, and/or sensory stimulator(s) 16 shown in FIG. 1. In this example, detection component 30 may be configured to detect arousal in subject 12 using EEG signals 402. Arousals are high frequency events that can be observable in the EEG signals 402, which indicate that the subject is waking up. If no arousal is detected at 404, and a slow wave sleep is detected at 412 in real-time, control component 32 is configured to control the sensory stimulator 401 to provide auditory stimulation to subject 12, and/or adjust the volume of the auditory stimulation to enhance the slow wave effect at 414. If detection component 30 detects arousal at 404 in subject 12 during stimulation period 406, control component 32 controls sensory stimulator 401 to stop the stimulation at 408. If the arousal is detected at 404 outside the stimulation period 406, control component 32 controls the sensory stimulator to delay the auditory stimulation at 410.

Figure 5A:
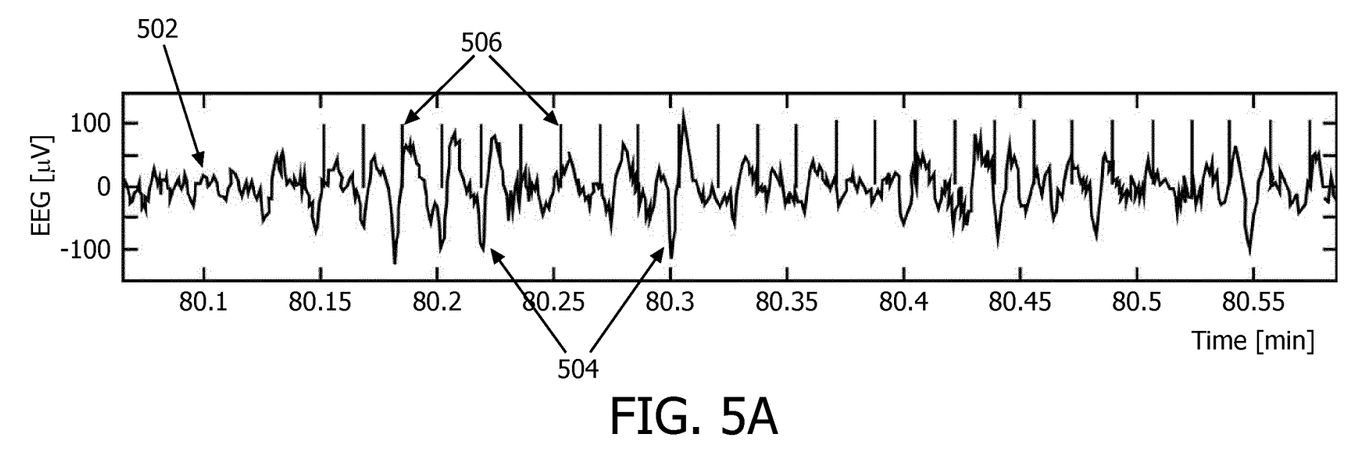
FIG. 5A shows example operations of the system delivering in-phase stimulation, in accordance with one or more embodiments.

In some embodiments, control component 32 (FIG. 1) may be configured to control stimulator(s) 16 (FIG. 1) to deliver stimulation to subject 12 at a desired phase of the detected slow waves (e.g., in-phase stimulation). In some embodiments, the desired phase corresponds to the up-state of the detected slow wave, and/or other phases of a slow wave. Control component 32 may be configured to control sensory stimulator(s) 16 to deliver sensory stimulation during the up-state of the detected slow waves. FIG. 5A shows an example of in-phase stimulation. FIG. 5A shows a portion of an EEG signal 502. The in-phase stimulation aligns the stimulation to a predetermined phase of the automatically detected slow-waves, in this example an up-state of the detected slow waves 504. A tone 506 is delivered for every detected slow wave 504.

Figure 5B:
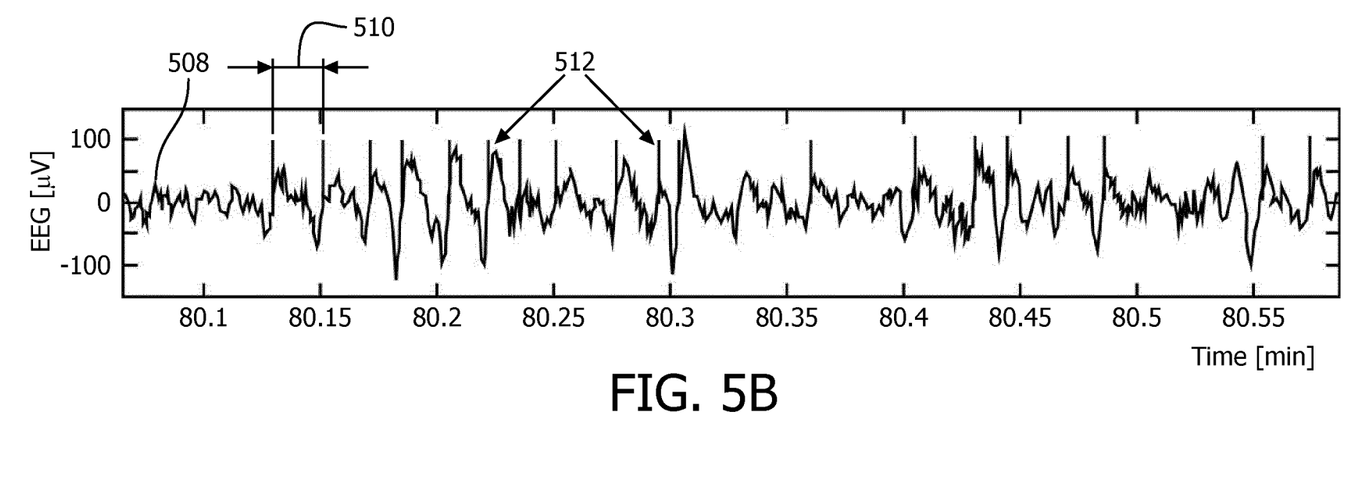
FIG. 5B shows an example of stimulation delivered at a fixed inter-tone stimulation interval, in accordance with one or more embodiments.

In some embodiments, control component 32 may be configured to control stimulator(s) 16 to deliver stimulation to subject 12 at a fixed inter-tone stimulation interval (ITI). In some embodiments, the fixed interval may be 1 second, and/or other intervals. FIG. 5B shows an example of stimulation delivered at a fixed inter-tone stimulation interval 510. 508 shows a portion of an EEG signal in a subject. Vertical lines 512 indicate the timing of the stimulation tones. In this embodiment, continuous or in-block stimulation is provided and the tones are separated from each other by a fixed ITI. The default ITI is set to 1 second because this approximate frequency corresponds to the hyperpolarization/depolarization oscillation of the cortical neuron's membrane potential. Such membrane potential oscillation is at the basis of the slow-wave events that are observed in the EEG.

Returning to FIG. 1, prediction component 34 is configured to predict timing for occurrence of one or more predicted slow waves. Prediction of timing for occurrence of one or more predicted slow waves may be based on the previously detected individual slow waves. In some embodiments, prediction of timing for occurrence of one or more predicted slow waves may be performed by estimating slow waves frequency. Slow-wave frequency may be continuously estimated by band-pass filtering the EEG signal in a narrow frequency band (e.g. 0.1 to 2 Hz) in which the frequency of predicted slow wave is expected to belong to, and using the Hilbert transform on the filtered signal to determine first the instantaneous phase of the signal, taking the time derivative, and averaging over a 1-minute long window to obtain a more stable estimate. Alternative manners to detect the instantaneous phase of the system include the Wavelet transform, and/or other techniques.

In some embodiments, responsive to not detecting the predicted slow wave at the predicted timing, control component 32 may be configured to control the one or more sensory stimulator(s) 16 to provide sensory stimulation to the subject. Sensory stimulation may be provided at the predicted timing for occurrence of the predicted slow wave. In some embodiments, prediction component 34 may be configured to predict timing of an up-state of the predicted slow wave. Control component 32 may be configured to sensory stimulator(s) 16 to provide stimulation at the timing of the predicted up-state responsive to not detecting a predicted slow wave.

By way of non-limiting example, in operation according to one or more embodiments, system 10 is configured to provide sensory stimulation to subject 10 at timings of detected slow waves. System 10 is further configured to predict timing of predicted slow waves based on the detected slow waves. In the event where system 10 does not detect a predicted slow wave at the predicted timing, system 10 provides sensory stimulation at the predicted timing of the predicted slow wave. In some embodiments, if system 10 does not detect a slow wave, system 10 is configured to deliver stimulation to subject 12 at a fixed inter-tone stimulation interval (ITI), such that the ITI is based on the timings of the predicted slow waves.

Figure 6:
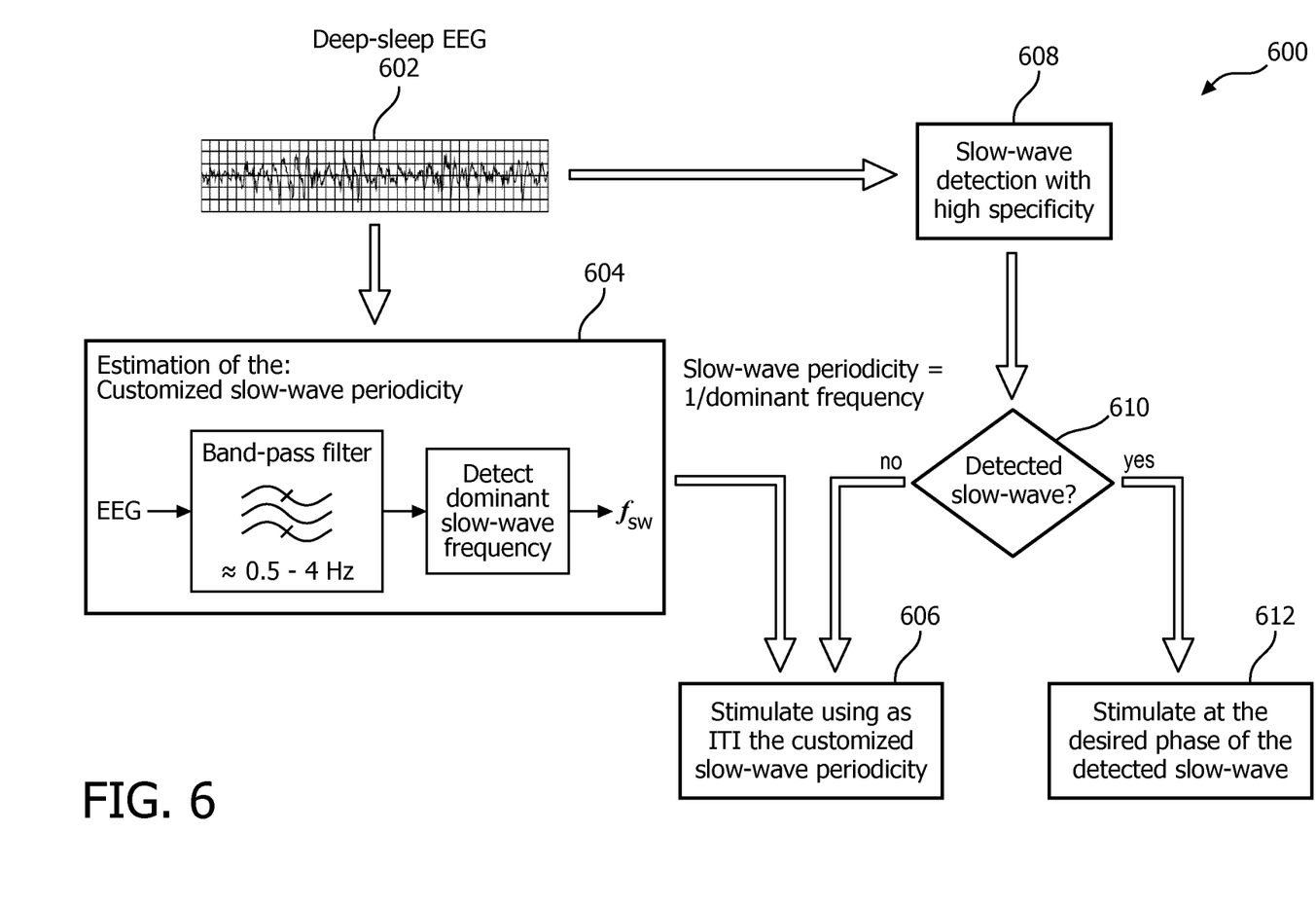
FIG. 6 illustrates example operations of the system delivering stimulation at detected slow waves timings and predicted slow waves timings, in accordance with one or more embodiments.

FIG. 6 illustrates example operations 600 of system 10. In the example shown in FIG. 6, detection component 30 detects slow waves with high specificity at 608 from a portion of an EEG 602. If a slow wave is detected at 610, control component 32 controls sensory stimulator(s) 16 to stimulate subject 12 at a desired phase of the detected slow wave at 612. If a slow wave is not detected at 610, control component 32 controls sensory stimulator(s) 16 to stimulate subject 12 at an ITI based on a customized slow wave periodicity at 606. The customized slow wave periodicity may be determined by prediction component at 604 based on the predicted timings of the predicted slow waves. In this example, the predicted timing of the predicted slow wave is determined based on determining the dominant slow wave frequency of the detected slow waves. In this example, the customized slow wave periodicity=1/dominant frequency.

Figure 7:
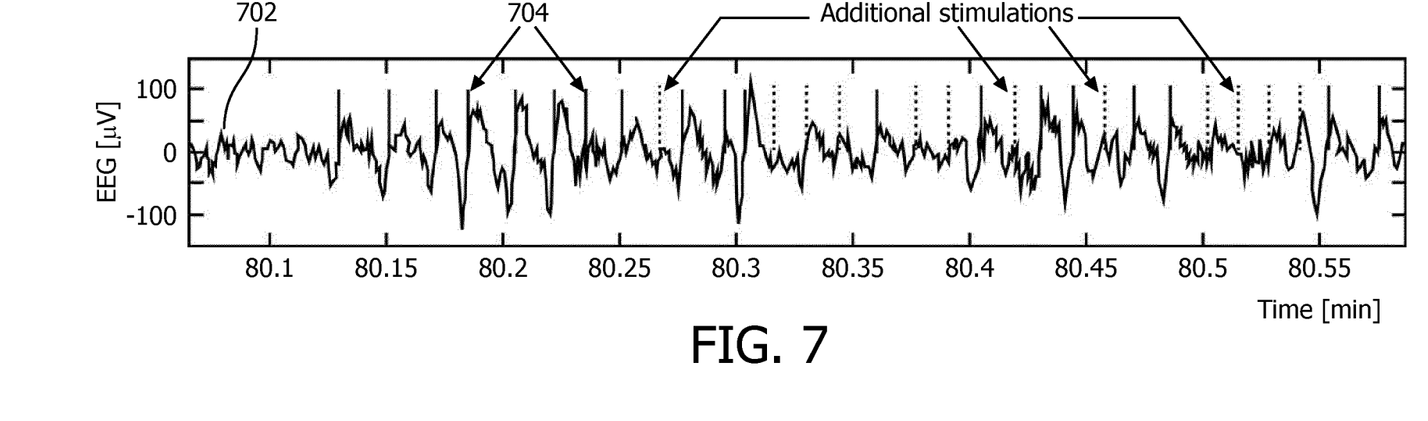
FIG. 7 illustrates providing stimulation at timing of detected slow waves and timing of predicted slow waves, in accordance with one or more embodiments.

FIG. 7 shows a portion of an EEG signal at 702 and sensory stimulations. FIG. 7 shows stimulation at an up-state of detected slow waves 704, and additional stimulations 706 at predicted timings of predicted slow waves.

Figure 8:
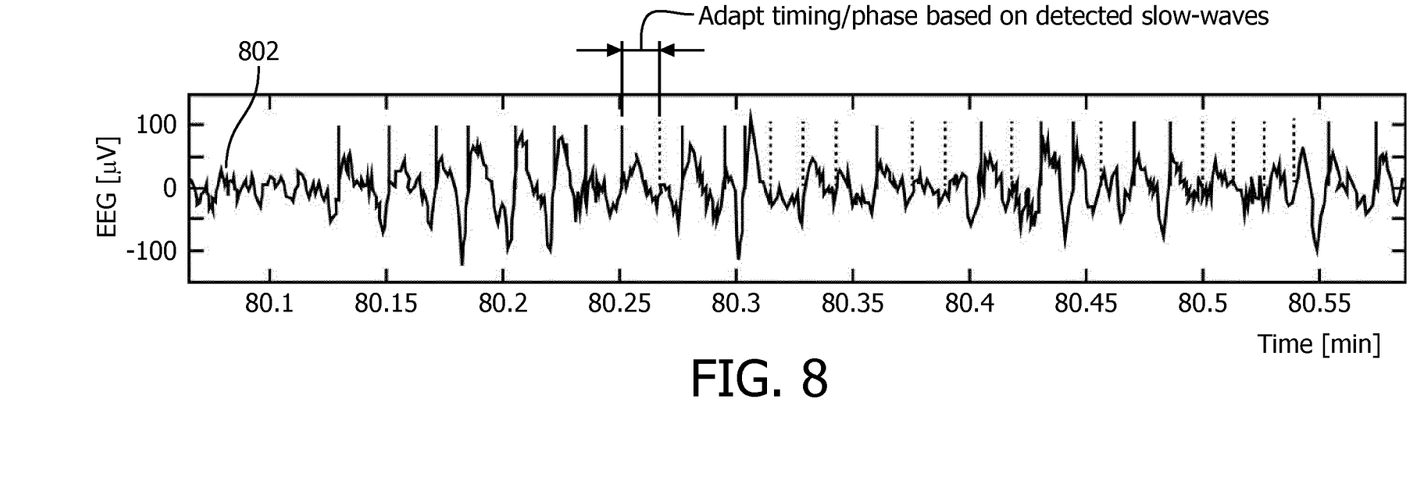
FIG. 8 illustrates sensory stimulation provided at the up-state of detected slow waves, and at the customized slow wave periodicity based on the detected slow waves.

FIG. 8 illustrates sensory stimulation provided at the up-state of detected slow waves, and at the customized slow wave periodicity based on the detected slow waves (as described above).

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical, charge-based storage media (e.g., EPROM, RAM, etc.), solid-state storage media (e.g., flash drive, etc.), and/or other electronically readable storage media. Electronic storage 22 may store software algorithms (e.g., adjustment algorithms used to adjust the baseline sleep state criteria), algorithm inputs (e.g., the baseline sleep state criteria), information determined by processor 20 (e.g., the adjusted sleep state criteria), information received via client computing platform(s) 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

Client computing platform(s) 24 is configured to provide an interface between system 10 and subject 12, and/or other users through which subject 12 and/or other users may provide information to and receive information from system 10. For example, client computing platform(s) 24 may display an EEG to a user. This enables data, cues, results, instructions, and/or any other communicable items, collectively referred to as "information," to be communicated between a user (e.g., subject 12, a doctor, a caregiver, and/or other users) and one or more of sensory stimulator(s) 16, processor 20, electronic storage 22, and/or other components of system 10.

Examples of interface devices suitable for inclusion in client computing platform(s) 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, client computing platform(s) 24 comprises a plurality of separate interfaces. In some embodiments, client computing platform(s) 24 comprises at least one interface that is provided integrally with processor 20, sensory stimulator(s) 16, sensor(s) 18, and/or other components of system 10.

Client computing platform(s) 24 may include one or more processors configured by machine-readable instructions to execute computer program components. The computer program components may be configured to enable one or more users associated with the client computing platform(s) 24 to interface with one or more component within or outside of system 10, and/or provide other functionality attributed herein to client computing platform(s) 24. By way of non-limiting example, client computing platform(s) 24 may include desktop computers, laptop computers, handheld computers, netbooks, tablets, smartphones, smartwatches, personal digital assistants (PDAs), cellular telephones, personal computers (PCs), and/or other computing platforms.

It is to be understood that other communication techniques, either hard-wired or wireless, are also contemplated by the present disclosure as client computing platform(s) 24. For example, the present disclosure contemplates that client computing platform(s) 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as client computing platform(s) 24 comprise, but are not limited to, an RS-232 port, RF link, an IR link, modem (telephone, cable or other). In short, any technique for communicating information with system 10 is contemplated by the present disclosure as client computing platform(s) 24.

In some embodiments, as shown in FIG. 1, system 10 may include one or more of stimulator(s) 16, sensor(s) 18, processor(s) 20, electronic storage 22, client computing platform(s) 24, and/or other components, all being communicatively coupled via a network 26.

The network 26 may include the Internet and/or other networks, such as local area networks, cellular networks, Intranets, near field communication, frequency (RF) link, Bluetooth™, Wi-Fi™, and/or any type(s) of wired or wireless network(s). Such examples are not intended to be limiting, and the scope of this disclosure includes embodiments in which stimulator(s) 16, sensor(s) 18, processor(s) 20, electronic storage 22, and/or client computing platform(s) 24 are operatively linked via some other communication media.

Figure 9:
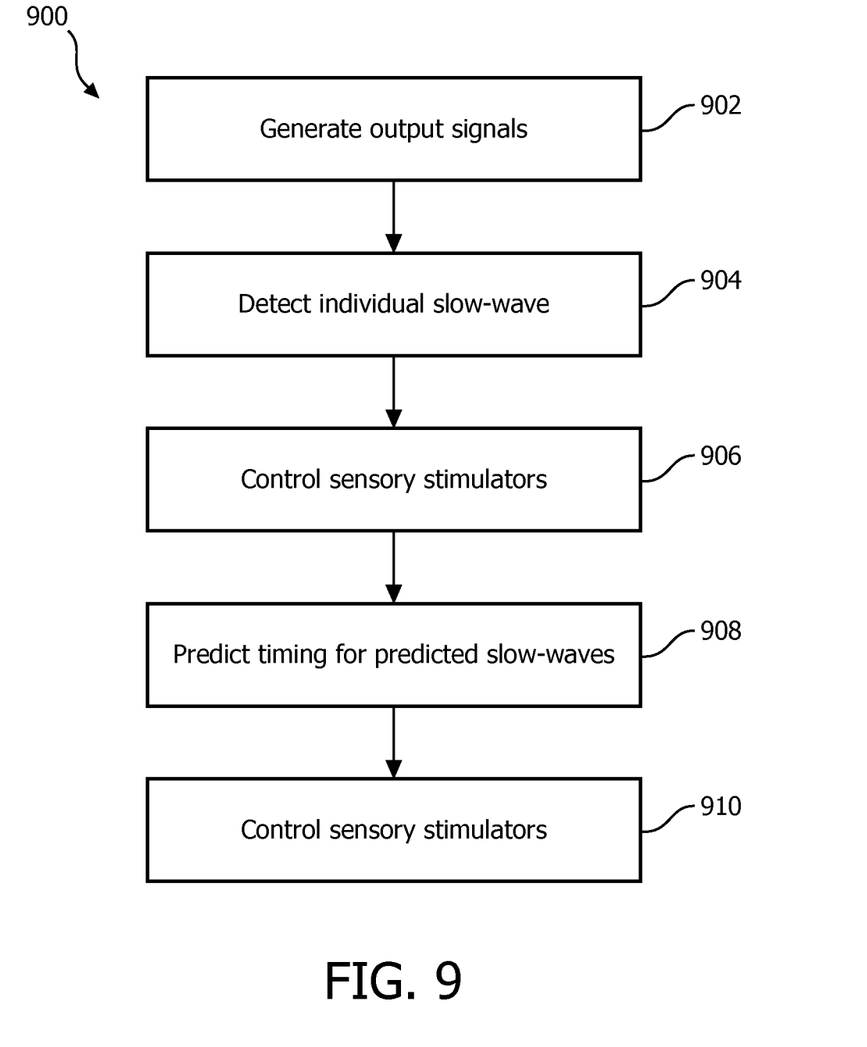
FIG. 9 illustrates a method for determining timing of sensory stimulation delivered to a subject during a sleep session with a determination system.

FIG. 9 illustrates a method 900 for determining timing of sensory stimulation delivered to a subject during a sleep session with a determination system. The system comprises one or more sensory stimulators, one or more sensors, one or more physical computer processors, and/or other components. The one or more processors are configured to execute one or more computer program components. The one or more computer program components may comprise one or more of a detection component 30, a control component 32, a prediction component 34, and/or other components. The operations of method 900 presented below are intended to be illustrative. In some embodiments, method 900 may be accomplished with one or more additional operations not described, and/or without one or more of the operations discussed. Additionally, the order in which the operations of method 900 are illustrated in FIG. 9 and described below is not intended to be limiting.

In some embodiments, method 900 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

At an operation 902, output signals conveying information related to brain activity of the subject during a sleep session are generated. In some embodiments, operation 902 is performed by one or more sensors the same as or similar to sensors 18 (shown in FIG. 1 and described herein).

At an operation 904, individual slow waves are detected in the subject. The individual slow waves may be detected based on the output signals. In some embodiments, operation 904 is performed by a computer processor component the same as or similar to detection component 30 (shown in FIG. 1 and described herein).

At an operation 906, sensory stimulators are controlled to provide sensory stimulation to the subject with a timing based on the detected individual slow waves. In some embodiments, operation 906 is performed by a computer processor component the same as or similar to control component 32 (shown in FIG. 1 and described herein).

At an operation 908, a timing for occurrence of a predicted slow wave is predicted. The timing for occurrence of the predicted slow wave may be detected based on the previously detected individual slow waves. In some embodiments, operation 908 is performed by a computer processor component the same as or similar to prediction component 34 (shown in FIG. 1 and described herein).

At an operation 910, responsive to not detecting the predicted slow wave at the predicted timing, the one or more sensory stimulators are controlled to provide sensory stimulation to the subject at the predicted timing for occurrence of the predicted slow wave. In some embodiments, operation 910 is performed by a computer processor component the same as or similar to comparison component 36 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

The invention claimed is:

1. A system configured to provide sensory stimulation to a subject during a sleep session, the system comprising:
   one or more sensory stimulators configured to provide sensory stimulation to the subject;
   one or more sensors configured to generate output signals conveying information related to brain activity of the subject; and
   one or more physical computer processors configured by computer-readable instructions to:
      detect individual slow waves in the subject based on the output signals;
      control the one or more sensory stimulators to provide sensory stimulation to the subject with a timing based on the detected individual slow waves;
      predict a timing for occurrence of a predicted slow wave based on previous ones of the detected individual slow waves; and
      responsive to not detecting the predicted slow wave at the predicted timing, control the one or more sensory stimulators to provide sensory stimulation to the subject at the predicted timing for occurrence of the predicted slow wave.

2. The system of claim 1, wherein the one or more physical computer processors are further configured, by computer-readable instructions, to determine an up-state of the detected individual slow waves and to control the one or more sensory stimulators to deliver sensory stimulation during the up-state.

3. The system of claim 1, wherein the one or more physical computer processors are further configured, by computer-readable instructions, to:
   predict timing of an up-state of the predicted slow wave; and
   control the one or more sensory stimulators to provide stimulation at the timing of the predicted up-state responsive to not detecting the predicted slow wave.

4. The system of claim 1, wherein the one or more physical computer processors are further configured, by computer readable instructions, such that detecting individual slow waves, providing sensory stimulation, predicting a timing for occurrence of a predicted slow wave, and/or providing sensory stimulation to the subject at the predicted timing occur in real or near-real time during a sleep session of the subject.

5. The system of claim 1, wherein the one or more physical computer processors are further configured, by computer-readable instructions, to estimate an effect of sensory stimulation on a sleep state of the subject in real or near-real time and to control the one or more sensory stimulators to adjust the sensory stimulation based on the estimated effect on the subject.

6. A method for providing sensory stimulation to a subject during a sleep session with a determination system, the system comprising one or more sensory stimulators, one or more sensors, and one or more physical computer processors, the method comprising:

generating, with the one or more sensors, output signals conveying information related to brain activity of the subject;

detecting, with the one or more processors, individual slow waves in the subject based on the output signals;

controlling, with the one or more processors, the one or more sensory stimulators to provide sensory stimulation to the subject with a timing based on the detected individual slow waves;

predicting, with the one or more processors, a timing for occurrence of a predicted slow wave based on previous ones of the detected individual slow waves; and responsive to not detecting the predicted slow wave at the predicted timing, controlling the one or more sensory stimulators, with the one or more processors, to provide sensory stimulation to the subject at the predicted timing for occurrence of the predicted slow wave.

7. The method of claim 6, further comprising:

determining, with the one or more processors, an up-state of the detected individual slow waves; and controlling, with the one or more processors, the one or more sensory stimulators to deliver sensory stimulation during the up-state.

8. The method of claim 6, further comprising:

predicting, with the one or more processors, timing of an up-state of the predicted slow wave; and controlling, with the one or more processors, the one or more sensory stimulators to provide stimulation at the timing of the predicted up-state responsive to not detecting the predicted slow wave.

9. The method of claim 6, wherein the one or more processors are configured such that detecting individual slow waves, providing sensory stimulation, predicting a timing for occurrence of a predicted slow wave, and/or providing sensory stimulation to the subject at the predicted timing occur in real or near real time during a sleep session of the subject.

10. The method of claim 6, further comprising:

estimating, with the one or more processors, an effect of sensory stimulation on a sleep state of the subject in real or near-real time; and controlling, with the one or more processors, the one or more sensory stimulators to adjust the sensory stimulation based on the estimated effect on the subject.

11. A system configured to provide sensory stimulation to a subject during a sleep session, the system comprising:

means for providing sensory stimulation to the subject;

means for generating output signals conveying information related to brain activity of the subject;

means for detecting individual slow waves in the subject based on the output signals;

means for controlling the means for providing sensory stimulation to provide sensory stimulation to the subject with a timing based on the detected individual slow waves; and means for predicting a timing for occurrence of a predicted slow wave based on previous ones of the detected individual slow waves; wherein responsive to not detecting the predicted slow wave at the predicted timing, said means for controlling is further configured to control the means for providing sensory stimulation to provide sensory stimulation to the subject at the predicted timing for occurrence of the predicted slow wave.

12. The system of claim 11, wherein the means for detecting individual slow waves are further configured to determine an up-state of the detected slow waves and control the means for providing sensory stimulation to deliver sensory stimulation during the up-state.

13. The system of claim 11, wherein the means for predicting a timing for occurrence of the predicted slow wave is further configured to:

predict timing of an up-state of the predicted slow wave; and control the means for providing sensory stimulation to provide stimulation at the timing of the predicted up-state responsive to not detecting the predicted slow wave.

14. The system of claim 11, wherein detecting individual slow waves, providing sensory stimulation, predicting a timing for occurrence of a predicted slow wave, and/or providing sensory stimulation to the subject at the predicted timing occur in real or near-real time during a sleep session of the subject.

15. The system of claim 11, further configured to estimate an effect of sensory stimulation on a sleep state of the subject in real or near-real time, and controlling the means for providing sensory stimulation to adjust the sensory stimulation based on the estimated effect on the subject.

* * * * *